United States Patent
Pintschovius et al.

[11] 3,957,846
[45] May 18, 1976

[54] MONOSTYRYL-NAPHTHALENE DERIVATIVES

[75] Inventors: Ulrich Pintschovius, Hattersheim; Erich Schinzel, Hofheim, Taunus; Günter Rösch, Altenhain, Taunus, all of Germany

[73] Assignee: Hoechst Aktiengesellschaft, Frankfurt am Main, Germany

[22] Filed: Mar. 22, 1974

[21] Appl. No.: 453,848

Related U.S. Application Data

[62] Division of Ser. No. 206,175, Dec. 8, 1971, Pat. No. 3,822,305.

[30] Foreign Application Priority Data

Dec. 8, 1970 Germany............................ 2060228

[52] U.S. Cl................................................ 260/465 D
[51] Int. Cl.². ....................................... C07C 121/64
[58] Field of Search................................. 260/465 D

[56] References Cited
UNITED STATES PATENTS 3,514,495  5/1970  Ruby.............................. 260/465 X
3,689,481  9/1972  Scheuermann et al. ........ 260/465 X

*Primary Examiner*—Lewis Gotts
*Assistant Examiner*—Dolph H. Torrence
*Attorney, Agent, or Firm*—Connolly and Hutz

[57] ABSTRACT

Compounds of the formula

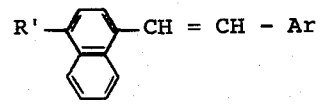

wherein R' is carboxy, lower carboalkoxy or lower carboalkoxy substituted by lower dialklamino or lower trialkylammonium and Ar is phenyl substituted by cyano, carboxy or lower carboalkoxy. These compounds show a characterized fluorescence when dissolved and are suitable for the optical brightening of different organic materials such as lacquers or synthetic fibres, for example fibres made of acetyl cellulose, polyesters, polyolefines, polyvinyl chloride or polyvinylidene chloride and films, foils, ribbons or shaped articles made from these materials.

3 Claims, No Drawings

MONOSTYRYL-NAPHTHALENE DERIVATIVES

This application is a division of application Ser. No. 206,175 filed Dec. 8, 1971, now U.S. Pat. No. 3,822,305.

The present invention relates to monostyryl derivatives, to a process for preparing them and to their use as optical brighteners.

It is already known how to prepare di-styryl compounds of naphthalene, wherein the naphthalene nucleus is substituted each time by styryl radicals in the positions 1.5 or 2.6 (German Offenlegungsschrift No. 1 900 537). Moreover, it is known to use these di-styryl-naphthalene compounds for the optical brightening of high-molecular-weight or low-molecular-weight organic materials or to use them as scintillators for different purposes in photography or for supersensibilization.

The present invention relates to monostyryl-naphthalene compounds, which are colorless or slightly yellow and have in dissolved form a violet blue to greenish blue fluorescence and whch correspond to the formula (I)

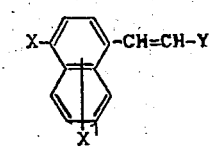
(I)

wherein X is hydrogen or a group attracting electrons, as for example a COOM group, M being a colorless cation, preferably hydrogen, an alkali metal or an ammonium ion, or a functional derivative of a carboxylic acid group, such as a carboxylic acid ester, carboxylic acid amide or nitrile group, a $SO_3M$-group, M having the above meaning, or a functional derivative of a sulfo group, as for example a sulfonamido, sulfonic acid alkyl or aryl ester group, or an alkyl sulfonyl radical, wherein the alkyl radical may be substituted, if desired, X has the same meaning as X and Y is a carbocyclic or heterocyclic aromatic radical, such as a phenyl-, α- or β-naphthyl-, biphenyl-, thienyl-, furyl- or pyridyl radical, which may be substituted by radicals attracting electrons, such as a COOM-group or functional derivatives of a carboxylic acid group, such as carboxylic acid ester, carboxylic acid amide or nitrile groups, acyl groups, $SO_3M$-groups, or functional derivatives of a sulfonic acid group, as for example sulfonamido, sulfonic acid alkyl or aryl ester groups, dialkylamino or trialkyl-ammonium radicals, or alkylsulfonyl radicals, which contain, if desired, one or several further substituents; the naphthalene radical as well as the carbocyclic or heterocyclic aromatic radical Y may be substituted by further non-chromophoric substituents, such as lower alkyl groups, halogen atoms, lower alkoxy groups, acylamino groups or the trifluoromethyl group.

The terms "lower alkyl", "lower alkoxy" and the like are intended to cover such aliphatic groups having generally 1 to 4 carbon atoms.

From the compounds embraced by the general formula (I), there are interesting above all the compounds corresponding to the general formula (II)

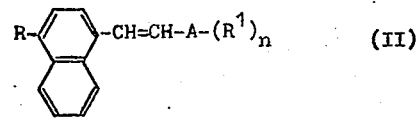
(II)

wherein A is a phenylene or naphthylene radical and R and $R^1$ represent, independently from one another, a hydrogen atom, a COOM-group, M being as defined above, or a functional derivative of a carboxylic acid group, such as a carboxylic acid ester group $COOR^2$, $R^2$ representing an optionally substituted phenyl radical or a straight-chained or branched, preferably lower alkyl group, which may contain further substituents, such as a dialkylamino, trialkyl ammonium or an alkoxy group, a carboxylic acid amide group $CO-NR^3R^4$, wherein the radicals $R^3$ and $R^4$ independently from each other may represent hydrogen atoms or lower optionally substituted alkyl groups or jointly with the nitrogen atom a hydroaromatic heterocyclic ring, a nitrile group; furthermore an acyl group $-CO-R^5$, in which $R^5$ stands for an optionally substituted lower alkyl or phenyl radical, a $SO_3M$-group, M having the above-mentioned meanings, or a functional derivative of a sulfo group, such as the sulfonic acid ester group $SO_2OR^2$, wherein $R^2$ is as defined above, a sulfonamide group $SO_2-NR^3R^4$, wherein $R^3$ and $R^4$ are as defined above; moreover a sulfonyl radical $SO_2R^6$, wherein $R^6$ stands for a lower straight-chained or branched alkyl group or an optionally substituted phenyl radical, which may contain further substituents, as for example a dialkylamino, trialkyl ammonium, acylamino or sulfo group; furthermore a trialkyl ammonium group containing preferably lower alkyl radicals or a lower alkoxy radical, and n is an integer of from 1 to 3, preferably from 1 or 2.

There are preferably used compounds of the formula (IIa)

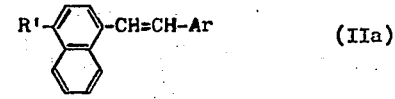
(IIa)

wherein R' is hydrogen, a group of the formula COOM, M being as defined above, the nitrile group or a low-molecular-weight carboalkoxy group, especially the carbomethoxy group and Ar is a naphthalene radical or a mono-nuclear aromatic residue. This residue is above all the phenyl, the pyridyl, the furyl and the thienyl radical. The radical Ar is preferably substituted by halogen, especially chlorine atoms, lower alkyl or alkoxy groups, lower trialkyl ammonium groups, low-molecular-weight alkanoylamino radicals, lower carboalkoxy groups, carboxy or sulfo groups and their alkali and ammonium salts, the nitrile group or a phenyl group. Up to two of these substituents are preferably bound to the mononuclear aromatic substance Ar.

The monostyryl naphthalene derivatives of the general formula (I) and (II) may be prepared in analogy to known processes:

A well-suited preparation process for example consists in reacting 1 mole of a naphthalene compound of the general formula (III)

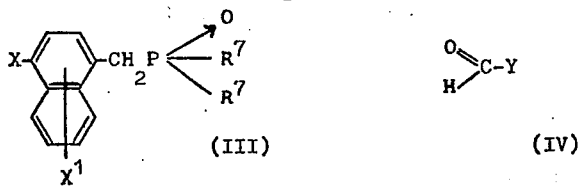

with 1 mole of a carbonyl compound (IV) or inversely 1 mole of a compound of the formula (V)

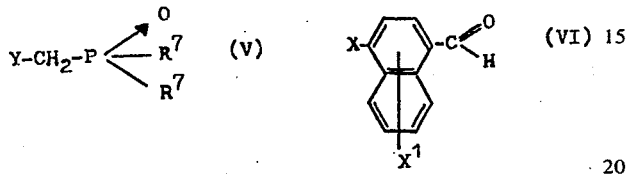

with 1 mole of a carbonyl compound (VI) (the so-called HORNER reaction). In the mentioned formulae X, X¹ and Y have the meaning given in the general formula (I), and R⁷ stands for identical or different alkyl, cycloalkyl, aralkyl or aryl radicals, optionally bound to the phosphorous atom by an oxygen atom. Inasmuch as the phosphorus-organic moiety carrying the radicals R⁷ are split off the chemical native of said groups is of no significance as to the reaction product. Preferred are, however, phenyl, cyclohexyl or lower alkyl residues.

The reaction products may be submitted to known conversions, which — starting for example from molecules containing sulfo or carboxy groups — lead to compounds having functional derivatives of sulfo or carboxy groups; moreover to sulfonations, sulfochlorinations and acylations.

The phosphorus compounds of the formula (III) and (V) necessary as starting materials are known and may be obtained for example by reacting halogeno-methyl, preferably chloro- or bromo-methyl compounds of the general formula (VII) and (VIII)

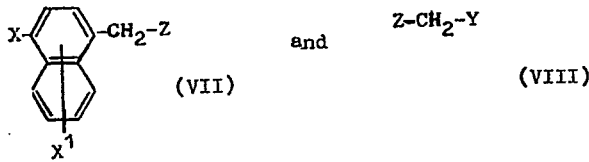

wherein Z stands for a halogen atom, with phosphorus compounds of the formula $R^7_2P$-O-alkyl.

The process is preferably carried out in inert solvents, for example hydrocarbons such as toluene and xylene, or alcohols such as methanol, ethanol, isopropanol, butanol, glycol, glycol ethers such as 2-methoxyethanol, hexanol, cyclohexanol, cyclooctanol, moreover in ethers such as diisopropyl ether, dioxane, tetrahydrofurane, furthermore in formamide and N-methyl-pyrrolidone. Particularly suitable are polar organic solvents such as dimethyl formamide (in the following referred to as "DMF") and dimethyl sulfoxide ("DMSO").

As condensing agents there are considered strongly basic compounds, such as alkali or alkaline earth metal hydroxides, alkali or alkaline earth metal alcoholates, alkali or alkaline earth metal amides, preferably potassium hydroxide, sodium hydroxide, potassium-tert.-butylate or sodium methylate, furthermore the alkali metal compounds of the dimethyl sulfoxide (alkali metal dimethyl sulfoxylates) and alkali hydrides.

Depending on the type of the starting materials, the reaction temperature ranges between about 10° and about 100°C, preferably between 20°C and 40°C.

For preparing the compounds according to the invention, the following aldehydes of the general formulae (IV) and (VI) are for example suitable:

4-Carboxy-benzaldehyde, 4-carbomethoxy-benzaldehyde, 2-cyano-benzaldehyde, 4-cyano-benzaldehyde, 3-cyano-benzaldehyde, 2-sulfo-benzaldehyde, benzaldehyde-2,4-disulfonic acid, benzaldehyde-2-sulfonic acid phenyl ester, α- and β-naphthaldehyde, biphenyl-4-aldehyde, 4'-carboethoxy-biphenyl-4-aldehyde, thiophene-2-aldehyde, 5-cyano-thiophene-2-aldehyde, furfural, pyridine-4-aldehyde, 4-carbomethoxy-1-naphthaldehyde, 4-cyano-1-naphthaldehyde, 4-carboxy-1-naphthaldehyde or 4-sulfo-1-naphthaldehyde.

As phosphorus compounds (III) and (V) the following compounds may be used for example: 1-diethoxy-phosphono-methyl-4-cyano-naphthalene, 1-dimethoxy-phosphono-methyl-4-cyano-naphthalene, 1-dimethoxy-phosphono-methyl-4-carbomethoxynaphthalene, 4-cyano-benzyl-phosphonic acid dimethyl ester, 4-cyano-benzyl-phosphonic acid diethyl ester, 3-cyano-benzyl-phosphonic acid dimethyl ester, 2-cyano-benzyl-phosphonic acid dimethyl ester, or 4-carbomethoxy-benzyl-phosphonic acid dimethyl ester.

Using the mentioned starting materials, the following compounds may be prepared for example according to the process described:

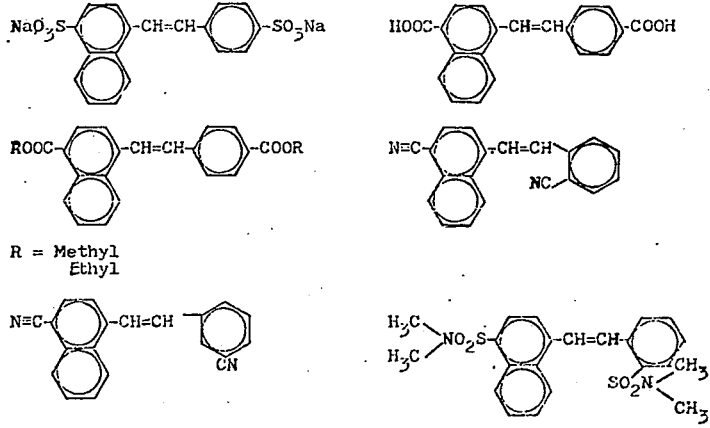

-continued
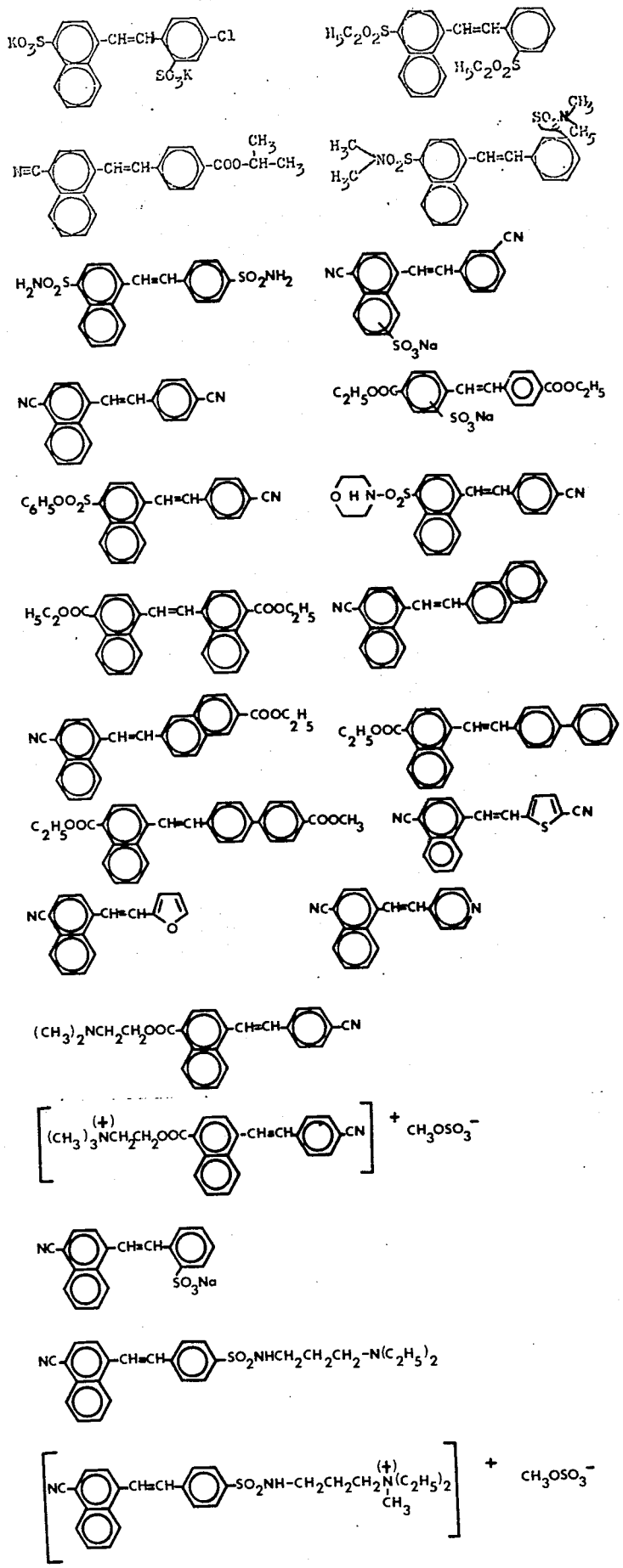

The compounds according to the invention show in dissolved form a more or less characterized fluorescence and are suitable for the optical brightening of different organic materials.

Good results are obtained for example when brightening lacquers or synthetic fibres, for example fibres made of acetyl cellulose, polyesters, polyolefins, polyolefines, chloride or polyvinylidene chloride and of films, foils, ribbons or shaped articles made from these materials.

The compounds of the invention which are soluble in water whereby the active (fluorescent) part of the molecule forms an anion are particularly suitable for the optical brightening of native and regenerated cellulose fibres, of wool and synthetic polyamide fibres. They show on these materials excellent degrees of whiteness; on wool and polyamide fibres they are preferably applied in the acidic medium at pH values ranging between about 3 and about 6. On cellulose fibres, the brilliance of the white shades obtained may generally be further increased by adding an electrolyte.

The compounds according to the invention are characterized by their resistance to sodium chlorite bleaching solutions. The use of said "anionically" soluble compounds combined with the application of sodium chlorite as bleaching agent make it possible to obtain on cellulose and polyamide fibres excellent degrees of whiteness. The whole may be carried out either at temperatures ranging below the boiling point of the water or under the so-called "high temperature" conditions.

The water-soluble compounds according to the invention may be used in dissolved form in organic solvents or in an aqueous dispersion, preferably by means of a dispersing agent. As dispersing agents there may be used for example soaps, polyglycol ethers of fatty alcohols, of fatty amines or alkyl phenols; cellulose sulfite waste liquors or condensation products of optionally alkylated naphthalene sulfonic acids with formaldehyde.

The compounds according to the invention may also be added to high-molecular-weight organic materials before or while these materials are shaped. Thus, they may be added to the molding material in the preparation of films, foils, ribbons or molded substances or before spinning in the spinning mass. Suitable compounds may be added to the low-molecular-weight starting materials before polycondensation, as in the case of polyamide-6, polyamide-6,6, linear polyesters of the polyethylene glycol terephthalate type, or before polymerization.

Compounds according to the invention substituted by one or preferably two carboxy or carboalkoxy groups may be incorporated into linear polyester molecules or synthetic polyamides by an ester or amide bond, if they are added under suitable conditions to these materials or preferably to their starting materials. Brighteners fixed in this manner in the substrate by a chemical bond are characterized by an extremely high fastness to sublimation and to solvents.

The compounds according to the invention soluble in water whereby the active part of the molecule forms a cation are particularly suitable for the optical brightening of mixed polymers having a minimum content of about 85% of polyacrylonitrile. They show on these materials excellent degrees of whiteness; on polyacrylonitrile fibres they are preferably applied in the acidic medium, at pH values of from about 2 to about 6, preferably from about 3 to about 4.

Due to their resistance to sodium chlorite bleaching solutions, it is possible to obtain with said "cationally" soluble compounds, combined with sodium chlorite as bleaching agents, excellent degrees of whiteness on polyacrylonitrile fibres. In this case the operation may also be carried out either at temperatures ranging below the boiling point of the water or under high-temperature conditions.

The amounts of the compounds of the general formula (I) to amount used according to the invention, calculated on the weight of the material to be optionally brightened, may vary within wide limits depending on the field of application and the effect desired. It may be easily determined by preliminary experiments and generally ranges between about 0.01 and 2%.

The compounds according to the invention may also be used in mixtures with dyestuffs, chemical bleaching agents, finishing agents, softening agents, detergents and laundry softening agents.

The following Examples serve to illustrate the invention.

EXAMPLE 1

At an internal temperature of not more than 40°C, a solution of 25 g of 4-cyano-benzaldehyde (92%) and 45.9 g of 4-diethoxy-phosphono-methyl-1-naphthonitrile in 100 ml of dimethylformamide (DMF) was introduced into a suspension of 39.4 g of potassium hydroxide (powder, 85%) in 120 ml of DMF; the whole had to be cooled slightly. After 1 hour, the reaction mixture was introduced while stirring into 1 liter of water and the pH-value was reduced to 8.5 with 29 ml of concentrated hydrochloric acid. The yellow deposit was filtered and washed with water. After drying 42 g of a crude product (100% of the theory) were obtained. By repeated recrystallization from glycol monomethyl ether (250 ml) under the addition of active charcoal and bleaching earth, the pure 1-(p-cyano-styryl)-4-cyano-naphthalene of the formula (101)

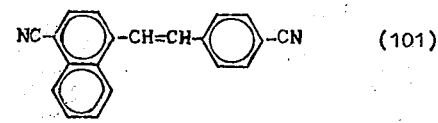

was obtained as greenish yellow crystals having a melting point of 205°–206°C.

Preparation of 4-diethoxy-phosphono-methyl-1-naphthonitrile: At first the 4-methyl-1-naphthonitrile was brominated in the side chain with N-bromo-succinimide according to M. J. S. DEWAR and P. J. GRISDALE, Am. Soc. 84, 3539 (1962).

36.9 g of 4-bromomethyl-1-naphthonitrile (melting point: 155° to 156°C) were slightly refluxed in 200 ml of xylene with 50 ml of triethyl phosphite using a packed column while the internal temperature increased from 124° to 133°C. Finally, the triethyl phosphite and xylene in excess were distilled off at last in vacuo. 45.9 g of a residue which crystallized slowly, was obtained. The 4-diethoxy-phosphono-methyl-1-naphthonitrile of the formula (102)

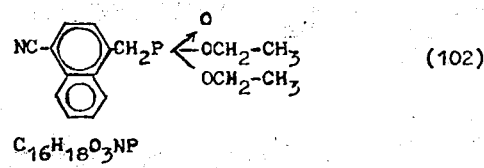

$C_{16}H_{18}O_3NP$ may be employed without difficulty for the condensation described above.

EXAMPLE 2

16 g of sodium methylate (in the form of a powder) were suspended in 100 ml of DMF. At a temperature of up to 30°C, a solution of 28.5 g of 4-formyl-benzoic acid methyl ester (99%) and 41.1 g of 4-dimethoxy-phosphono-methyl-1-naphthonitrile in 120 ml of DMF was added while cooling. After 30 minutes 35 g of glacial acetic acid were added. The reaction mixture was introduced into 1 liter of water, the resulting deposit was suction-filtered, washed and dried. 38 g of the crude product were obtained, which were dissolved in 7.5 l of chloroform. A small amount of carboxylic acid formed during the process was filtered. The cyano-ester was obtained by evaporating and purified by repeated recrystallization from toluene under addition of active charcoal and bleaching earth. The product of the formula (103)

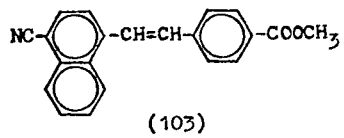

was obtained as greenish yellow crystals having a melting point of 189° to 190°C.

The 4-dimethoxy-phosphono-methyl-1-naphthonitrile of the formula (104)

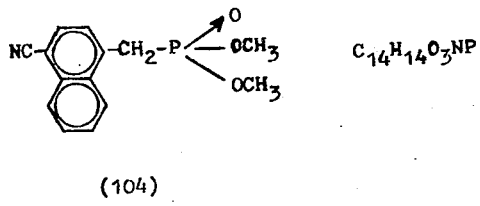

was prepared in analogy to the diethoxy compound from 36.9 g of 4-bromomethyl-1-methyl-1-naphthonitrile and 50 ml of trimethyl phosphite in 200 ml of xylene.

EXAMPLE 3

41.6 g of 4-dimethoxy-phosphono-methyl-1-naphthoic acid methyl ester and 28.5 g of 4-formyl benzoic acid methyl ester were dissolved in 150 ml of DMF. At an internal temperature of up to 35°C, this solution was introduced into a suspension of 16 g of sodium methylate in 100 ml of DMF. After 15 minutes 35 ml of glacial acetic acid were added. The reaction mixture was poured into 1 liter of water. After having suction-filtered, washed and dried, 33.2 g of the crude product of the formula (105)

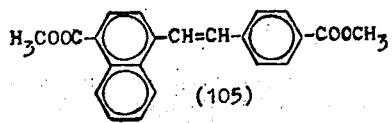

were obtained, which was stirred with an aqueous ammonia solution while heating for a short time up to 80°C.

By recrystallization from toluene, nearly colorless small crystals having a melting point of 153° to 154°C were obtained.

Preparation of 4-dimethoxy-phosphono-methyl-1-naphthoic acid methyl ester: 4-methyl-1-naphthoic acid methyl ester was converted into the 4-bromomethyl-1-naphthoic acid methyl ester (melting point: 84° to 85°C, nearly colorless crystals from methanol) by heating with N-bromo-succinimide in tetrachloromethane.

37 g of 4-Bromomethyl-1-naphthoic acid methyl ester were boiled for 4 hours with 50 ml of trimethyl phosphite and 200 ml of xylene. Then the trimethyl phosphite and the xylene in excess were distilled off. 41.6 g of a residue of 4-dimethoxy-phosphono-methyl-1-naphthoic acid methyl ester of the formula (106) were obtained

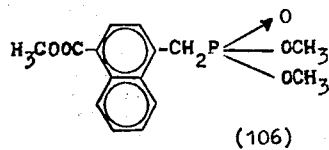

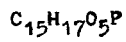

which remained in the liquid form and could be used without further purification.

EXAMPLE 4

63.1 g of 4-dimethoxy-phosphono-methyl-1-naphthoic acid methyl ester and 32 g of 4-cyano-benzaldehyde were dissolved in 200 ml of DMF and added to a suspension of 24 g of sodium methylate in 150 ml of DMF at an internal temperature of up to 35°C while cooling. After 15 minutes 52 ml of glacial acetic acid were added. The reaction product was introduced into 1 liter of water, suction-filtered, washed and dried whereby 62.0 g of crude product (96% of the theory) were obtained. A small amount of carboxylic acid formed as by-product was reconverted into the methyl ester by heating with thionyl chloride and finally by boiling in methanol. By repeated recrystallization from toluene, the 4-(p-cyano-styryl)-1-naphthoic acid methyl ester of the formula (107)

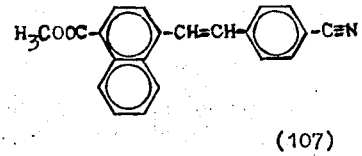

was obtained in yellow crystals having a melting point of 165° to 166°C.

EXAMPLE 5

At temperatures of up to 40°C, a solution of 46 g of 4-diethoxy-phosphono-methyl-1-naphthonitrile and 28 g of diphenyl-4-aldehyde was added to a suspension of 30 g of potassium hydroxide (about 85%, powdered form) in 120 ml of DMF. After stirring for half an hour at 40°C the reaction mixture was introduced into 1 liter of water. After having suction-filtered, washed and dried, 45.9 g (87% of the theory) of the crude product of the formula (108)

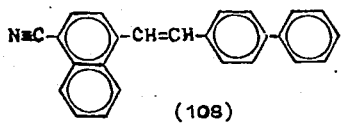
(108)

were obtained, which could be purified by recrystallization from n-butanol to form slightly yellow crystals having a melting point of 169°–170°C.

The compounds listed in the following Table could be prepared in analogous way:

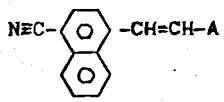

| No. | A | crude yield (% of the th.) | mp. °C | solvents used for purification |
|-----|---|---|---|---|
| 109 | –⟨O⟩ | 97 | 115–116,5 | butanol |
| 110 | –⟨O⟩–Cl | 97 | 155–156 | butanol |
| 111 | –⟨O⟩–O–CH₃ | 88,5 | 151–151,5 | butanol |
| 112 | –⟨O⟩–N(CH₃)₂ | 67 | 164–166 | methoxyethanol |
| 113 | –⟨O⟩–NH–C(O)–CH₃ | 81 | 247–248 | DMF |
| 114 | –⟨O⟩N | 80 | 159–160 | butanol |
| 115 | –⟨S⟩–C≡N | 93 | 207–208 | ethoxyethane |

EXAMPLE 6

At an internal temperature of not more than 40°C, a solution of 41.0 g of 4-dimethoxy-phosphono-methyl-1-cyano-naphthalene and 34.3 g of the sodium salt of benzaldehyde-2-sulfonic acid (about 84.2% determined as free sulfonic acid) in 120 ml of DMF was added to a suspension of 24 g of sodium hydroxide (powder, about 98%), and stirring was continued for 1 hour. The reaction mixture was introduced into 1 liter of water and the pH-value was adjusted to 7.0 with 33 ml of concentrated hydrochloric acid. The mixture was filtered at 80°C and the product precipitated with 130 g of sodium chloride. The sodium sulfonate was suction-filtered and washed with a 10% NaCl solution. 39.2 g of a yellowish powder (7% NaCl content) having the following structure was obtained:

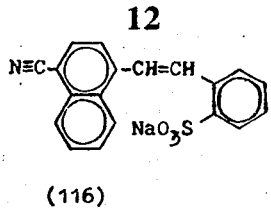
(116)

EXAMPLE 7

A solution of 41.5 g of 4-dimethoxy-phosphono-methyl-1-cyano-naphthalene and 57.7 g of benzaldehyde-2,4-disulfonic acid (87.5%, in form of the Na-salt) in 120 ml of DMF was added to the NaOH suspension prepared according to Example 6; after one hour the reaction mixture was poured into 0.23 l of water, the pH-value was adjusted to 7.0 with 26 ml of concentrated hydrochloric acid; a solution of

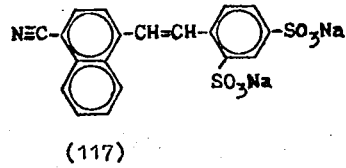
(117)

was obtained, which could only be obtained by evaporating due to its good solubility. The substance was extracted with hot glycol monomethyl ether. After evaporating the solvent, the product was obtained as a greenish yellow crystal powder (content: 65%).

EXAMPLE 8

At temperatures below 30°C, a solution of 38.3 g of p-cyano-benzyl-phosphonic acid diethyl ester and 33.5 g of 4-cyano-naphthaldehyde in 150 ml of DMF was added while cooling with ice to a suspension of 16 g of sodium hydroxide (powder, about 98%) in 100 ml of DMF, and stirring was continued for 15 minutes. The reaction mixture was introduced while stirring into 1 liter of water and worked up as described in Example 1. 33.5 g of the crude product were obtained. By further purification the 1-(p-cyano-styryl)-4-cyano-naphthalene of the formula (101) referred to in Example 1 was obtained in greenish-yellow crystals having a melting point of 205° to 206°C.

The p-cyano-benzyl-phosphonic acid diethyl ester was obtained by refluxing of 22.7 g of p-cyano-benzyl chloride and 50 ml of triethyl phosphite in 200 ml of DMF for 6 hours using a column and subsequent concentration in vacuo as a colorless viscous oil (which could not be crystallized) of the formula (118)

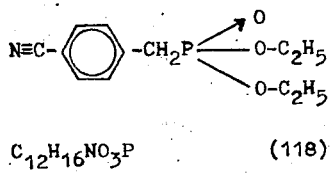

$C_{12}H_{16}NO_3P$ (118)

EXAMPLE 9

According to the method described in Example 8, the 1-(p-cyano-styryl)-naphthalene of the formula (119)

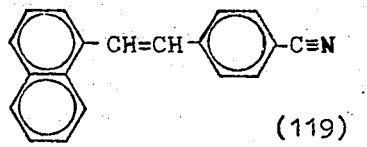

was obtained from 38.3 g of p-cyano-benzyl-phosphonic acid diethyl ester and 23.5 g of α-naphthaldehyde in 150 ml of DMF as light yellow crystals having a melting point of 130° to 131°C.

EXAMPLE 10

15.7 g of the compound (107) were boiled for 10 minutes in 0.5 liter of ethanol with a solution of 2.08 g of sodium hydroxide (98%) in 4.5 g of water. The main amount of ethanol was distilled off and replaced by water. After filtration 14.1 g of 4-[p-cyano-styryl]-1-naphthoic acid of the formula (120)

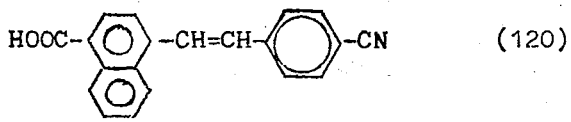

were precipitated with 5 ml of glacial acetic acid as a nearly colorless crystal powder having a melting point of from 300° to 302°C.

EXAMPLE 11

According to the method described in Example 10, the 4-[p-carboxy-styryl]-1-naphthoic nitrile of the formula (121)

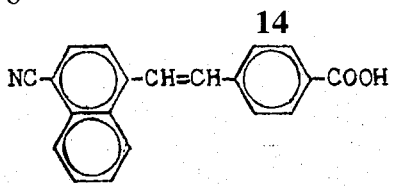

was obtained from the compound (103) in a 97% yield as small greenish yellow crystals having a melting point of 306° to 307°C.

EXAMPLE 12

By saponification with sodium hydroxide solution in excess in ethanolic solution and precipitation with hydrochloric acid the corresponding dicarboxylic acid of the formula (122)

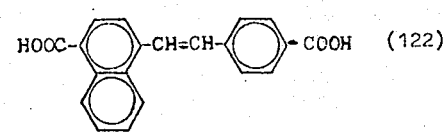

was obtained from compound (105) as a greenish yellow powder having a melting point of 342° to 343°C.

EXAMPLE 13

59.6 g of 1-[p-dimethylamino-styryl]-4-cyano-naphthalene (112) were refluxed for 2 hours in 240 ml of chlorobenzene (anhydrous) with 27 g of dimethyl sulfate. A yellow substance was separated which was suction-filtered after cooling and washed with acetone. 82 g (96.6% of the theory) of the ammonium salt of the formula (123)

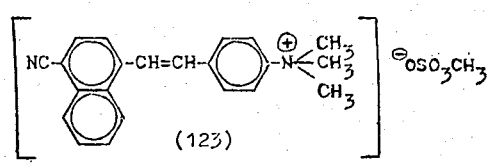

were obtained, the melting point ranging between 243° and 247°C (decomposition).

EXAMPLE 14

38.4 g of compound (114) were refluxed with 400 ml of chlorobenzene and 20.2 g of dimethyl sulfate, the precipitated ammonium salt was suction-filtered after cooling and washed with acetone. 55.6 g (97% of the theory) of a greenish yellow powder of a decomposition range of from 252° to 258°C (development of gas) of the formula (124)

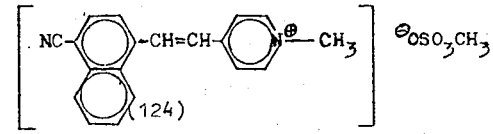

were obtained.

EXAMPLE 15

While cooling externally to 30°C, a solution of 21.5 g of 4-formyl-1-naphthoic acid methyl ester and 31 g of 4-dimethoxy-phosphono-methyl-1-naphthoic acid methyl ester in 100 ml of DMF was added to a suspension of 12 g of sodium methylate in 80 ml of DMF. After stirring for 10 minutes, the condensation was finished by adding 25 ml of glacial acetic acid, and the reaction mixture was poured into 1 liter of water. The suction-filtered deposit was stirred at 70°C with a mixture of 2 ml of a 25% $NH_3$ solution and 0.5 l of water, suction-filtered, washed with water and dried.

33.8 g of a greenish yellow powder of the formula (125)

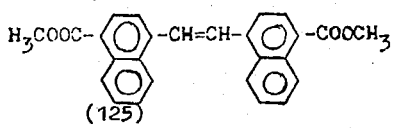

was obtained which had after repeated recrystallizations from chlorobenzene or DMF a melting point of from 222° to 223°C.

EXAMPLE 16

A fabric bleached in usual manner made of polyethylene glycol terephthalate filaments, which had a slight yellowish shade was treated for half an hour at 98°C with an aqueous dispersion, containing 0.1 g/l of the compound (101) at a goods-to-liquor-ratio of 1 : 20. The fabric showed an excellent white shade.

EXAMPLE 17

A raw fabric of polyethylene glycol terephthalate was treated at a goods-to-liquor-ratio of 1 : 20 in a bleaching bath which contained per liter 0.6 g of sodium chlorite (100%), 0.2 ml of glacial acetic acid, 0.2 ml of concentrated sulfuric acid and 0.1 g of compound (101). After raising the temperature slowly, it was maintained for 30 minutes at 80°–85°C and then for 30 minutes at 98°C. The white shade of the fabric was bright and clear.

EXAMPLE 18

A fabric of polyethylene glycol terephthalate filaments bleached in usual manner was impregnated with a dispersion of 5 g/l of compound (103) and squeezed between rollers, so that the fabric had still a liquid content of 60% of its dry weight, and then treated for 30 seconds with hot air of 190°C. After this treatment the fabric showed an excellent degree of whiteness.

EXAMPLE 19

1 kg of dimethyl terephthalate and 0.8 kg of glycol were melted under addition of 0.5 g of compound (105), 4 g of $TiO_2$ (as a dispersion in glycol), 0.2 g of manganese acetate and 0.12 g of phosphoric acid and transesterified by heating to 160° to 220°C, the methanol and a small amount of glycol being distilled off. After adding 0.3 g of antimonium trioxide, polycondensation took place in a nitrogen atmosphere while stirring and distilling off glycol. After comminuting, melting and spinning, polyester filaments having a high degree of whiteness were obtained, and the optical brightener had an excellent fastness to sublimation.

EXAMPLE 20

A fabric of cellulose triacetate was introduced into a bath at 50°C at a goods-to-liquor-ratio of 1 : 40, which contained 1 g/l of sodium chlorite and 0.05 g/l of compound (103). Formic acid was added to the bath until the pH-value was adjusted to 3.8. The bath was heated for 20 minutes to 98°C, the temperature was maintained for 1 hour and then slowly cooled. After rinsing the fabric optically brightened in this manner was characterized by an excellent degree of whiteness.

EXAMPLE 21

A fabric of polyamide fibres of the nylon-6 type was introduced into a bath at 60°C, the goods-to-liquor ratio being 1 : 30, which contained 0.15% of the brightener (107), calculated on the goods weight, as well as 0.8 ml of a 50% acetic acid, 1.2 g of sodium pyrophosphate and 1.8 g of sodium dithionite and heated for 30 minutes to 70°C. After rinsing and drying, an intense brightening was observed.

EXAMPLE 22

10 g of compound (120) were converted into the acid chloride in 100 ml of dioxane with 2.75 ml of thionyl chloride. After eliminating the thionyl chloride in excess by vacuum distillation the residue was dissolved again with dioxane and was stirred for 1 hour at 45°C with 3.2 g of β-dimethylaminoethanol and then introduced into a potassium carbonate solution. The product (which was slightly greasy) was suction-filtered and dried. The free base (melting point: 145°C; clear point: 153°C) was dissolved in 100 ml of warm ethyl acetate. After filtration the filtrate was stirred for 30 minutes with 2.75 g of dimethyl sulfate at 50°C. By suction-filtering at 10°C, washing with acetone and drying 7.8 g of compound (126)

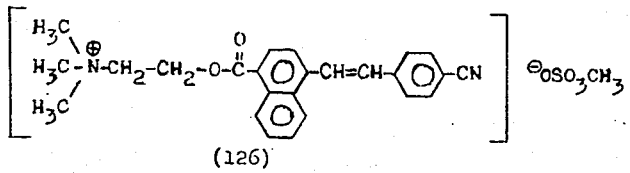

were obtained as a yellowish water-soluble powder (decomposition at 204°–218°C).

On a polyacrylonitrile fabric this product (126) provided also in the presence of sodium chlorite good white shades.

We claim:
1. A compound of the formula

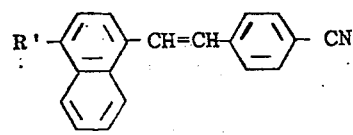

wherein R' is carboxy, lower carboalkoxy or lower carboalkoxy substituted by lower dialkylamino or lower trialkylammonium.

2. A compound, having the formula
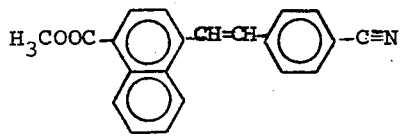
3. A compound, having the formula
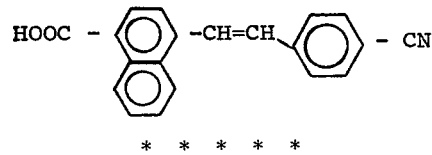
* * * * *